United States Patent [19]

Sweeney et al.

[11] Patent Number: 5,348,544
[45] Date of Patent: Sep. 20, 1994

[54] SINGLE-HANDEDLY ACTUATABLE SAFETY SHIELD FOR NEEDLES

[75] Inventors: Niall Sweeney, Rutherford, N.J.;
Peter W. Bressler, Philadelphia, Pa.;
Richard J. Caizza, Barry Lakes, N.J.

[73] Assignee: Becton, Dickinson and Company, Franklin Lakes, N.J.

[21] Appl. No.: 157,780

[22] Filed: Nov. 24, 1993

[51] Int. Cl.5 ................................................ A61M 5/32
[52] U.S. Cl. ................................ 604/192; 604/198; 128/919
[58] Field of Search ............... 604/192, 198, 263, 187, 604/110; 128/919

[56] References Cited

U.S. PATENT DOCUMENTS

| | | | |
|---|---|---|---|
| 3,840,008 | 10/1974 | Noiles . | |
| 4,735,618 | 4/1988 | Hagen | 604/192 |
| 4,790,828 | 12/1988 | Dombrowski et al. | 604/198 |
| 4,795,443 | 1/1989 | Permenter et al. | 604/198 |
| 4,826,490 | 5/1989 | Byrne et al. | 604/198 |
| 4,850,977 | 7/1989 | Bayless | 604/198 |
| 4,863,434 | 9/1989 | Bayless | 604/198 |
| 4,863,435 | 9/1989 | Sturman et al. | 604/198 |
| 4,863,436 | 9/1989 | Glick | 604/198 |
| 4,886,503 | 12/1989 | Miller | 604/192 |
| 4,887,998 | 12/1989 | Martin et al. | 604/110 |
| 4,898,589 | 2/1990 | Dolgin et al. | 604/198 |
| 4,904,244 | 2/1990 | Harsh et al. | 604/187 |
| 4,911,706 | 3/1990 | Levitt | 604/198 |
| 4,950,250 | 8/1990 | Haber et al. | 604/192 |
| 5,092,851 | 3/1992 | Ragner | 604/192 |
| 5,108,379 | 4/1992 | Dolgin et al. | 604/198 |
| 5,242,417 | 9/1993 | Paudler | 604/192 |

*Primary Examiner*—John D. Yasko
*Attorney, Agent, or Firm*—John L. Voellmicke

[57] ABSTRACT

A safety shield is provided for a medical implement having a needle cannula. The safety shield includes a guard that is slidably movable along the needle cannula from a proximal position where the tip of the needle cannula is exposed to a distal position where the tip of the needle cannula is safety shielded. A hinged arm connects the guard to a hub of the needle cannula or to the medical implement with which the needle cannula is used. The hinged arm can be collapsed upon itself, such that the guard is adjacent the hub of the needle cannula. Alternatively, the hinged arm can be extended to cause the guard to move distally along the needle cannula and into a position for shielding the tip of the needle cannula. A spring may be provided to assist movement of the guard toward the distal shielded position.

27 Claims, 8 Drawing Sheets

SINGLE-HANDEDLY ACTUATABLE SAFETY SHIELD FOR NEEDLES

FIELD OF THE INVENTION

The subject invention relates to single-handedly actuatable safety shields for hypodermic needles, blood collection needles, catheter needles and other medical implements to prevent accidental needle sticks.

DESCRIPTION OF THE PRIOR ART

Accidental sticks with a used needle cannula can transmit disease. As a result, most prior art needle cannulas have a safety shield. Some prior art safety shields define a rigid cap that can be telescoped in a proximal direction over the used needle cannula. This reshielding procedure requires the health care worker to hold the needle cannula and the associated medical implement in one hand and the shield in the other. A slight misalignment as the hands move toward one another may cause the accidental needle stick that the shield is intended to avoid. Additionally, many medical procedures require the application of pressure to the penetration site after the needle has been removed. Thus, health care workers often are unable to use both hands for shielding the needle cannula. In these situations, workers may merely deposit the used medical implement on a nearby surface, with the intention of completing the shielding at a more convenient time. However, the subsequent reshielding often is neglected and a contaminated needle may lie exposed in an area where people are working.

Some prior art needle shields are hingedly attached to the hub of the needle cannula. These prior art shields extend orthogonal to the needle cannula prior to and during use. After use, the shield is rotated 90° into a position where the needle cannula is protectively enclosed. Shields of this type can interfere with the usage of a hypodermic syringe or other medical instrument, and can visually obscure the tip of the needle cannula during use. An unobstructed view of the point of penetration is important for many medical procedures. In particular, the health care worker often will want to align the medical instrument with the bevel facing the worker as the needle cannula is inserted. This is difficult under the best of circumstances due the small diameter of the needle cannula. Problems of aligning the bevel are greater if the needle cannula is obscured by a large hingedly attached shield.

Some prior art hypodermic syringes include a shield telescoped around the needle cannula or around a longer-than-normal needle hub. The shield is advanced distally after the hypodermic syringe has been used. This prior art assembly with the shield telescoped on the needle hub is generally twice as long as a conventional needle, and can be cumbersome to use. Additionally, health care workers must use two hands to effect the shielding or must exhibit considerable manual dexterity to complete the needle shielding with one hand.

Some prior art safety shields have relied upon coil springs coaxially around the needle cannula to automatically move the shield. The shield may be locked in a proximal position with the coil spring compressed. Unlocking of the shield causes the coil spring to urge the shield distally into a shielded condition. However, it is generally undesirable to provide an apparatus with a small thermoplastic lock stored for a considerable period of time under the stress of a coil spring. This stored energy can cause plastic parts to deform, and may alter the performance of the shield.

SUMMARY OF THE INVENTION

The subject invention is directed to a safety shield mounted on or near a needle cannula. The safety shield includes a needle guard that can be moved from a first position where the tip of the needle cannula is exposed for use, to a second position where the tip of the needle cannula is substantially enclosed.

The safety shield of the subject invention also includes a hinged arm. The hinged arm may include a proximal segment and a distal segment articulated to one another. In this context, the term "distal" refers to locations further from the health care worker, and hence closer to the tip of the needle cannula. The term "proximal" refers to locations closer to the health care worker, and hence further from the tip of the needle cannula. The distal segment of the hinged arm is articulated to the needle guard, while the proximal segment of the hinged arm is articulated to a location spaced proximally from the tip of the needle cannula. For example, the proximal segment of the hinged arm may be articulated to the needle hub or to a distal portion of a syringe barrel or to an additional member which is attached to the syringe barrel and/or the needle hub. This proximal segment of the hinged 0 aria may be unitary with the needle hub, the syringe barrel or the additional element. Similarly, the distal segment of the hinged arm may be unitary with the needle guard.

The proximal and distal segments of the hinged arm are dimensioned to fold toward one another when the needle guard is near its proximal position. The segments of the hinged arm also are dimensioned to preferably extend into a substantially linear orientation when the needle guard safely encloses the tip of the needle cannula. Thus, over extension of the safety shield is prevented by limits imposed by the dimensions of the hinged arm.

The needle guard may comprise a rigid cap having a generally tubular side wall and a distal end wall extending transversely across the side wall. The distal end wall may have an aperture for slidably receiving the needle cannula. The cap and the hinged arm may be dimensioned to have the tip of the needle cannula safely engaged between the tubular side wall and the distal end wall of the cap when the hinged arm is in its extended position.

The needle guard may also include a clip, which is preferably metallic, engaged in the cap. A distal wall of the clip may be biased against the side of the needle cannula for sliding movement therealong. As the hinged arm reaches its fully extended position, the distal wall of the metallic clip in the cap will pass the tip of the needle cannula, and will biasingly move into a position where the distal wall of the metallic clip protectively covers the tip of the needle cannula.

The safety shield of the subject invention may include biasing means for urging the needle guard toward its distal position. The biasing means preferably is in a stable condition with little or no stored energy when the needle guard is in its proximal First position. The user of the safety shield may have to overcome forces exerted by the biasing means to urge the needle guard from its proximal position. This initial actuation may urge the biasing means into an orientation where the biasing means effectively propels the hinged arm into an extended condition, such that the needle guard covers the tip of the needle cannula. The biasing means preferably extends unitarily between the proximal segment of the hinged arm and either the needle hub, the syringe barrel or an element attached to the needle hub and/or the syringe barrel, and may define a portion of the hinged joint therebetween. For example, the biasing means may define an over-center hinged spring where stored energy accumulated during early stages of rotation propels the hinged components during later stages of rotation.

DETAILED DESCRIPTION OF THE PREFERRED EMBODIMENT

Figure 1:
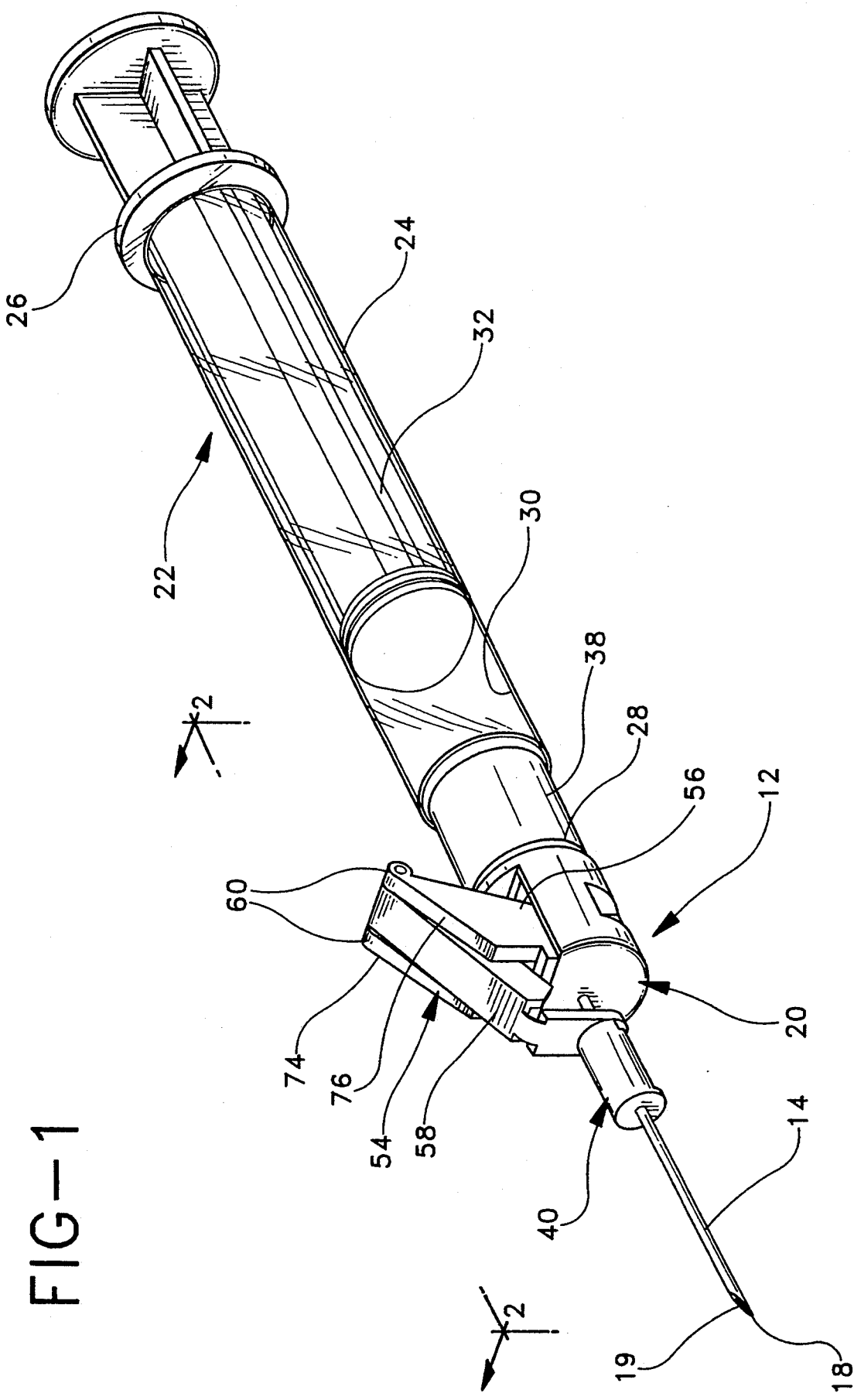
FIG. 1 is a perspective view of a hypodermic syringe having a needle shield in accordance with the subject invention.

A shieldable needle assembly in accordance with the subject invention is identified generally by the numeral 12 in FIGS. 1–5. Needle assembly 12 includes a needle cannula 14 having a proximal end 16, a distal tip 18 and a lumen 19 extending therebetween. Distal tip 18 in this embodiment includes a bevel aligned at an acute angle to the longitudinal axis of needle cannula 14.

Shieldable needle assembly 12 further includes a needle hub 20 which is securely and permanently engaged with proximal end 16 of needle cannula 14.

Figure 2:
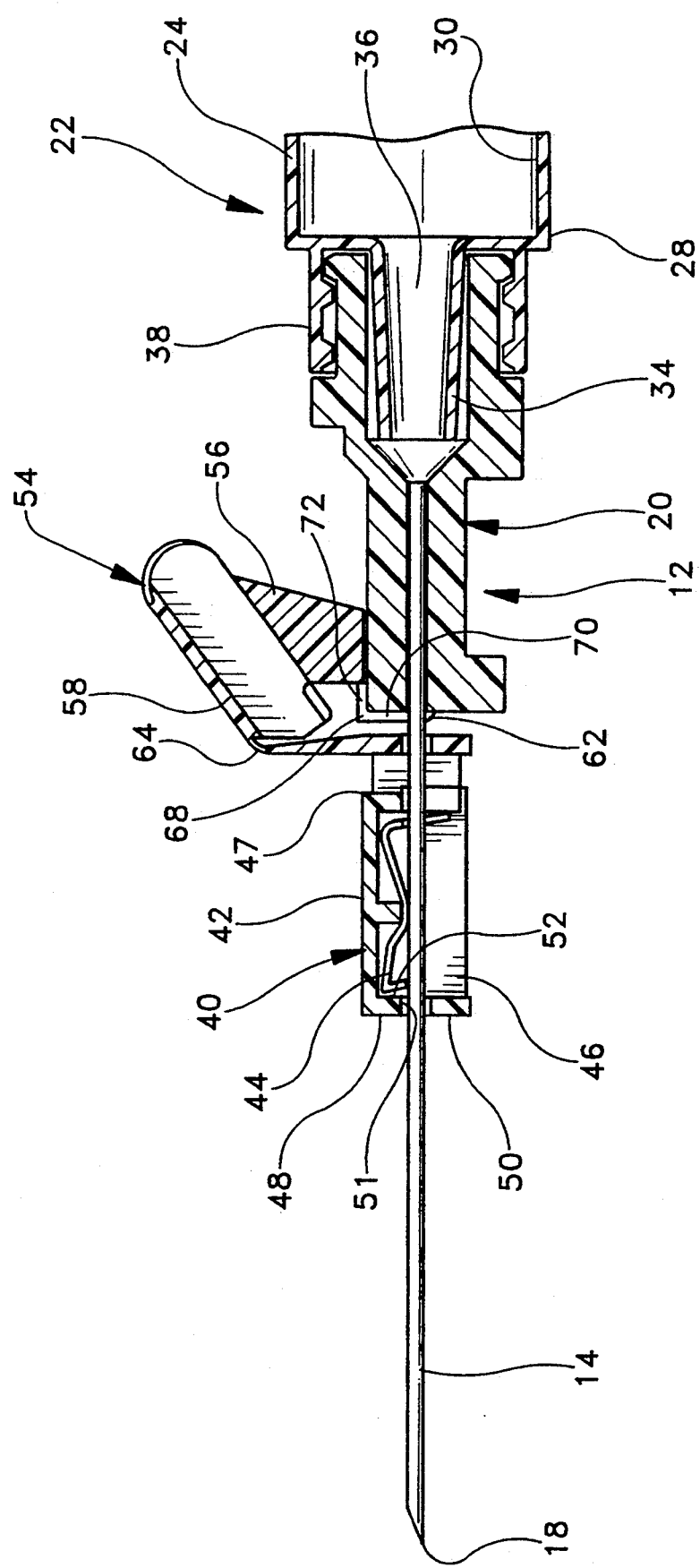
FIG. 2 is a cross-sectional view taken along line 2—2 of FIG. 1.

Needle assembly 12 is connected to a hypodermic syringe 22 as shown in FIGS. 1 and 2. The hypodermic syringe includes a syringe barrel 24 having opposed proximal and distal ends 26 and 28 respectively and a chamber 30 extending therebetween. Proximal end 26 of syringe barrel 24 is open and slidably receives a plunger 32. Distal end 28 of syringe barrel 24 includes an elongate tip 34 having a passage 36 extending therethrough. Distal end 28 of syringe barrel 24 preferably includes a luer collar 38 concentrically surrounding tip 34. The luer collar includes an array of internal threads 55 which may be engaged by needle hub 20 of shieldable needle assembly 12.

Tip 18 of needle cannula 14 may become contaminated after being placed in communication with a patient. Accidental sticks with a contaminated needle have been known to transmit diseases. Needle assembly 12, enables unimpeded use of needle cannula 14 and hypodermic syringe 22, and ensures effective shielding of tip 18 of needle cannula 14 immediately after withdrawal from a patient, as explained herein.

The preferred shieldable needle assembly 12 includes a guard 40 which comprises a cap portion 42 and a clip 44. As depicted most clearly in FIGS. 2–4, cap 42 is preferably molded from a thermoplastic material to include a cylindrically generated side wall 46, preferably extending circumferentially through more than 180°, and having opposed proximal and distal ends 47 and 48. Side wall 46 preferably is longer than the bevel at tip 18 of needle cannula 14. Cap 42 further includes an end wall 50 extending across distal end 48 of side wall 46. End wall 50 includes an aperture 51 which is slidable along needle cannula 14.

Figure 4:
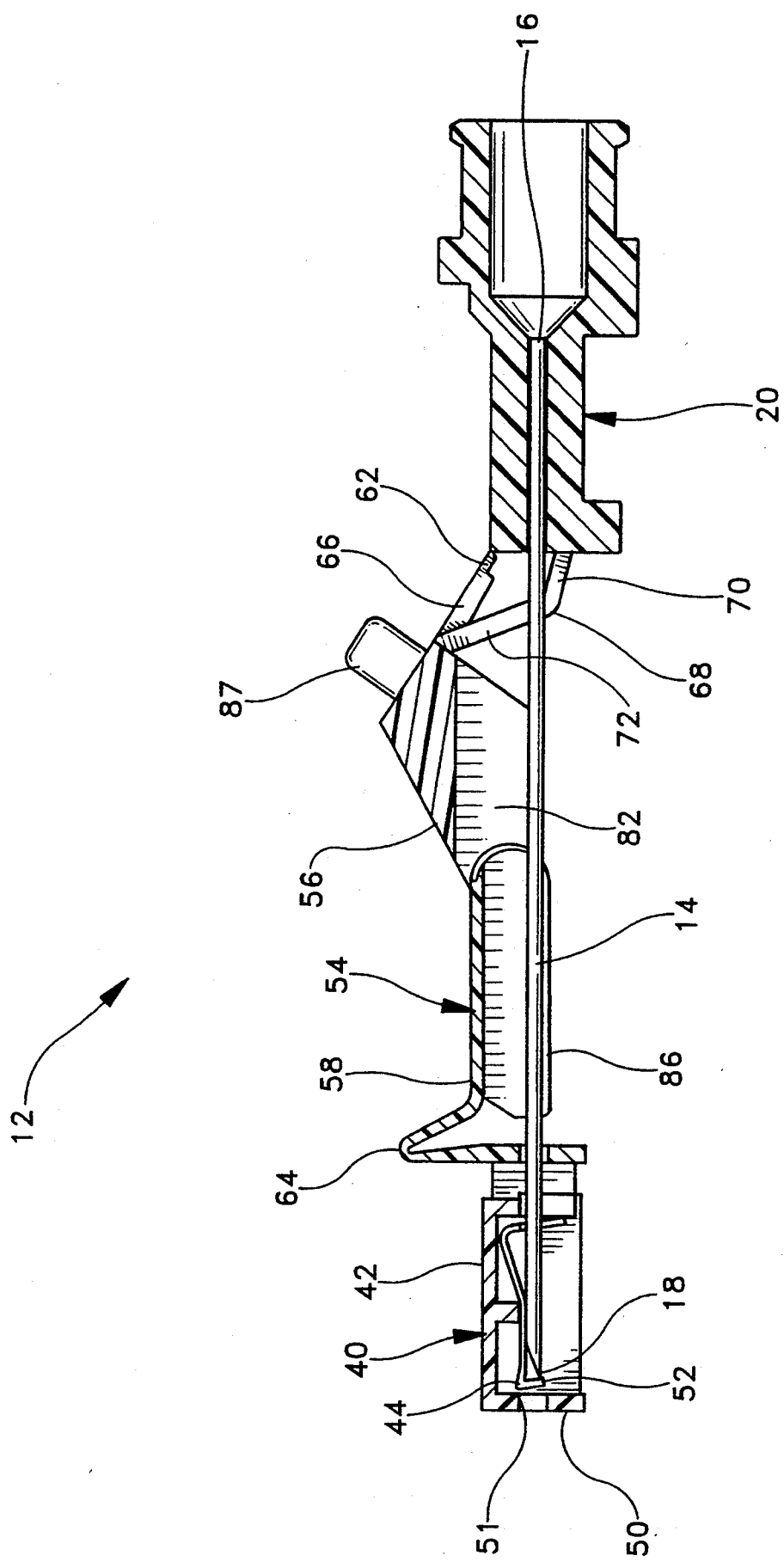
FIG. 4 is a cross-sectional view similar to FIGS. 2 and 3, but showing the needle shield in its fully extended condition and shielding the tip of the needle cannula.
Figure 5:
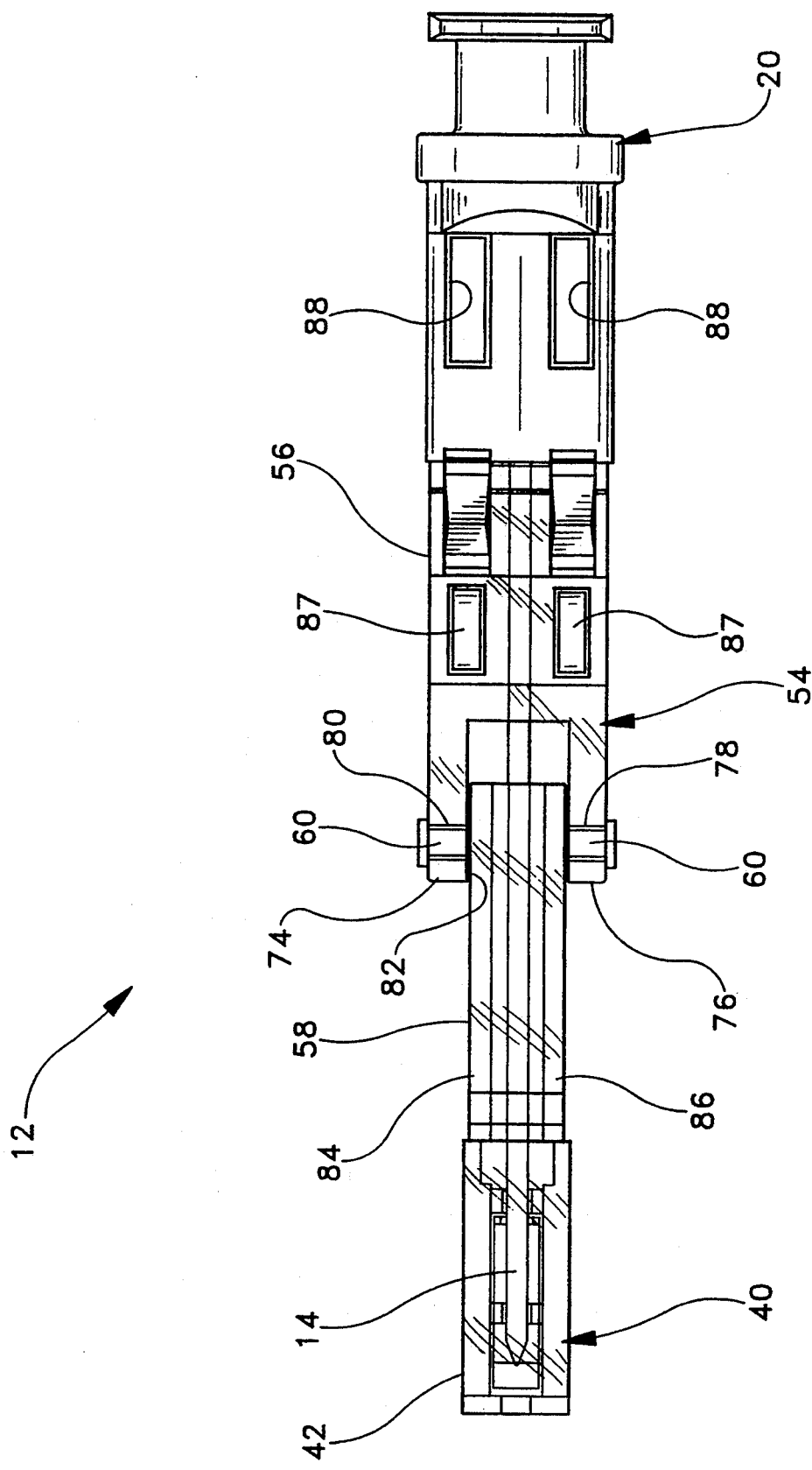
FIG. 5 is a side elevational view of the needle shield in the FIG. 4 orientation.

Clip 44 of needle guard 40 is retained between needle cannula 14 and cap 42. Clip 44 includes a distal wall 52 that is configured to be biased against needle cannula 14. However, sufficient distal movement of cap 42 will cause distal wall 52 of clip 44 to pass beyond tip 18 of needle cannula 14. Distal wall 52 of clip 44 will then be biased over tip 18 as illustrated in FIGS. 4 and 5 and as described further herein. Clip 44 is preferably made of metal such as stainless steel or other material exhibiting good penetration resistance. Clip 44 provides more protection against penetration by tip 18 than could be provided by the plastic of cap 42. Additionally, a clip made of metal or other puncture resistant material enables the plastic of the shieldable needle assembly to be selected in view of its resiliency and other performance characteristics, and without concern for the ability of the plastic to resist needle punctures.

Shieldable needle assembly 12 further includes a hinged arm assembly 54 having a proximal segment 56 and a distal segment 58 which are articulated to one another at hinge pins 60. Proximal segment 56 of hinged arm assembly 54 is articulated to needle hub 20 at proximal hinge 62. Distal segment 58 of hinged arm assembly 54 is articulated to cap 42 at distal hinge 64, which is adjacent proximal end 47 of side wall 46. Needle hub 20, cap 42 and hinged arm 54 may be unitary with one another. However, in the preferred embodiment shown herein proximal and distal segments 56 and 58 are snapped into engagement with one another through hinge pins 60.

Hinge 62 between needle hub 20 and proximal segment 56 of hinged arm assembly 54 is an over-center spring hinge. More particularly, hinge 62 includes substantially nonbiasing hinge member 66 and spring element 68. Nonbiasing hinge member 66 define the rotational path about which proximal segment 56 of hinged arm assembly 54 will rotate relative to needle hub 20. Spring element 68 in this preferred embodiment includes first and second segments 70 and 72 which are orthogonally aligned to one another in an unbiased condition, as shown in FIG. 2. However first and second segments 70 and 72 of spring element 68 can be resiliently deflected from the unbiased angle alignment into a more linear alignment.

Figure 3:
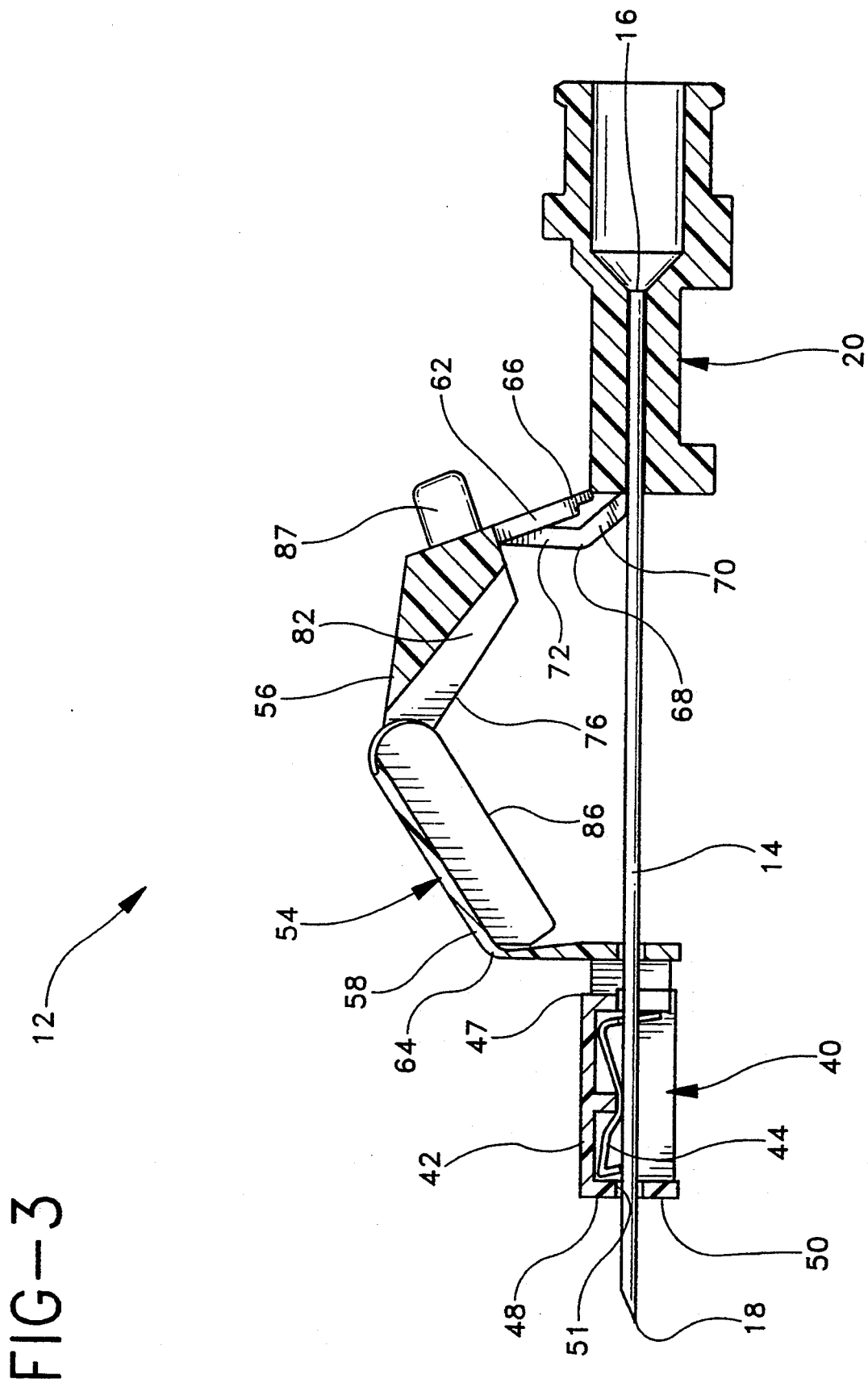
FIG. 3 is a cross-sectional view similar to FIG. 2, but showing the shield in a partly extended position.

Rotation of proximal segment 56 of hinged arm assembly 54 from the FIG. 2 alignment toward the FIG. 4 alignment will cause segments 70 and 72 of each spring element 68 to be deflected from the right angle condition shown in FIG. 2 toward a more linear orientation as shown in FIG. 3. The user of syringe 22 and needle assembly 12 must manually overcome the forces attributable to the resiliency of spring element 68 to move proximal segment 56 of hinged arm assembly 54 from the FIG. 2 orientation to the FIG. 3 orientation. The resiliency inherent in spring element 68 will urge the spring hinges back toward an undeflected right angle condition. This resiliency will effectively propel proximal segment 56 of hinged arm assembly 54 from the FIG. 3 orientation into the FIG. 4 orientation, with proximal segment 56 being adjacent needle cannula 14. Simultaneously, distal segment 58 will rotate into substantially parallel alignment with needle cannula 14, and guard 40 will slide distally toward tip 18.

As explained further herein, the self-propelling feature enabled by the hinge 62 is desirable and facilitates one-hand actuation of the needle shield 12. Equally important, however, is the fact that hinge 62 is in a stable condition in the FIG. 2 orientation with virtually no stored energy exerting pressure on the plastic components of a shieldable needle assembly 12. As noted above, stored energy acting on plastic can affect the reliability and performance of the part. In this instance, however, the stored energy is accumulated only after proximal segment 56 of hinged arm 54 is moved from the stable FIG. 2 orientation into the FIG. 3 orientation. The accumulated energy then performs work for the user and moves hinged arm assembly 54 toward the FIG. 4 orientation. Hinge 62 will again be stable with virtually no stored energy in the FIG. 4 orientation where the needle cannula 14 is safely shielded.

Another feature of the present invention is that the spring element will resist accidental or inadvertent pressure which would tend to force the guard toward the second position where the clip covers the end of the needle.

As shown in FIG. 1, proximal segment 56 of hinged arm assembly 54 includes a pair of parallel spaced apart flanges 74 and 76 which terminate at collinear bearing slots 78 and 80 respectively. The bearing slots are dimensioned to receive hinge pins 60 which in this embodiment are unitarily molded as part of distal segment 58 of hinged arm assembly 54. Flanges 74 and 76 define a channel 82 which receives distal segment 58 in the collapsed condition, as shown in FIGS. 1 and 2., and which receives a portion of needle cannula 14 in the extended condition of hinged arm 54 as shown in FIG. 4. Distal segment 58 of hinged arm assembly 54 also includes first and second parallel spaced apart side flanges 84 and 86 defining a cannula-receiving channel 88 therebetween.

As shown in FIGS. 1 and 2, distal segment 58 can be articulated about hinge pins 60 into a collapsed condition nested in channel 82 between flanges 74 and 76 of proximal segment 56. The relatively small dimensions of each segment 56 and 58, and the nesting of those segments in a collapsed condition substantially eliminates visual or physical obstruction of cannula 14 by hinged arm assembly 54. To the contrary, hinged arm assembly 54 preferably is aligned to define a plane which passes symmetrically through the bevel defining tip 18 of needle cannula 14. Thus, hinged arm assembly 54 can be used to achieve a desired alignment of the bevel prior to injection into a patient. If it is desirable to have the bevel of tip 18 facing upwardly, the user of syringe 22 need merely have the collapsed hinged arm assembly of FIGS. 1 and 2 point upwardly. Hinged am assembly 54 also can facilitate the initial threaded engagement of the small needle hub into luer collar 38 of syringe barrel 24. In this regard, the longitudinally extending flanges of both proximal and distal segments 56 and 58 add to the rigidity of hinged arm 54, and enable hinged arm 54 to be grasped and rotated for threadedly engaging needle hub 20 with luer collar 38.

After using syringe 22, proximal and distal segments 56 and 58 of hinged arm assembly 54 can be articulated about hinges 60, 62 and 64 toward an extended position, with guard 40 slidably telescoping along needle cannula 14 and away from needle hub 20.

This extension of hinged arm assembly 54 from the collapsed condition shown in FIG. 2 to the extended position shown in FIG. 4 can be generated entirely from locations proximally on needle cannula 14. More particularly, proximal segment 56 of hinged arm assembly 54 extends radially outwardly from needle cannula 14 sufficiently to define a proximally facing actuation surface extending transversely from syringe barrel 24. Thus, distally directed pressure by a finger of the hand engaging syringe barrel 24 will urge hinged arm assembly 54 from its collapsed condition to its extended condition, and will thereby urge guard 40 toward tip 18 of needle cannula 14.

Proximal and distal segments 56 and 58 of hinged arm assembly 54 are dimensioned to permit end wall 50 of cap 42 and end wall 52 of clip 44 to pass distally beyond tip 18 of needle cannula 14, as shown in FIG. 4. However, the respective lengths of proximal and distal segments 56 and 58 of hinged arm assembly 54 prevent complete separation of guard 40 from needle cannula 14. Additionally, the configuration of the metallic clip 44 causes tip 18 of needle cannula 14 to be biasingly trapped by clip 44. Portions of needle cannula 14 between needle hub 20 and cap 42 will be surrounded by flanges 74 and 76 of proximal hinge segment 56 and flanges 84 and 86 of distal hinge segment.

Another feature of the present invention involves lugs 87 and slots 88, as best illustrated in FIG. 5. When the shieldable needle assembly is in the position of FIG. 2, lugs 87 are positioned within slots 88 so that the device may withstand the torsional forces needed to attach it to a syringe luer fitting and remove it from a syringe luer fitting. Without the lugs and the slots the mechanism may be damaged through the act of twisting the hub onto and off of a syringe assembly.

As an alternative to the over-center hinge spring 62 of FIGS. 2–4, a separate coil spring may be provided. In particular, with reference to FIG. 6, a coil spring may extend from needle hub 20 to proximal segment 56. Coil spring 90 is stretched by moving hinged arm 54 from the FIG. 2 orientation to the FIG. 3 orientation. Coil spring 90 then resiliently contracts and urges the needle guard distally over tip 18 of needle cannula 14, substantially as explained in the preceding embodiment.

Figure 7:
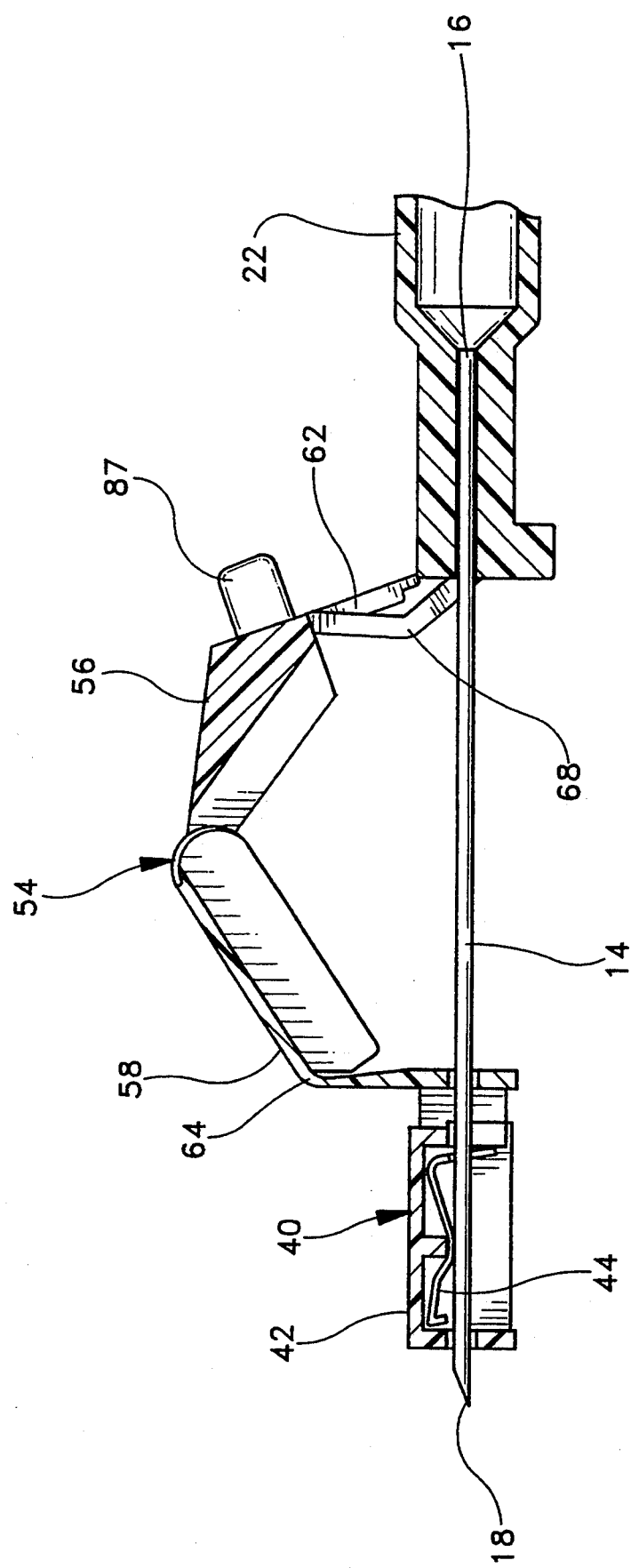
FIG. 7 is a cross-sectional view similar to FIG. 3, but showing the needle shield connected directly to the syringe barrel.

FIG. 7 shows still another optional design where proximal segment 56 of hinged arm assembly 54 is articulated directly to syringe barrel 22. In all significant respects, this embodiment performs like the embodiments and illustrated above. This embodiment, however, is appropriate for hypodermic syringes having an integral needle cannula.

Figure 6:
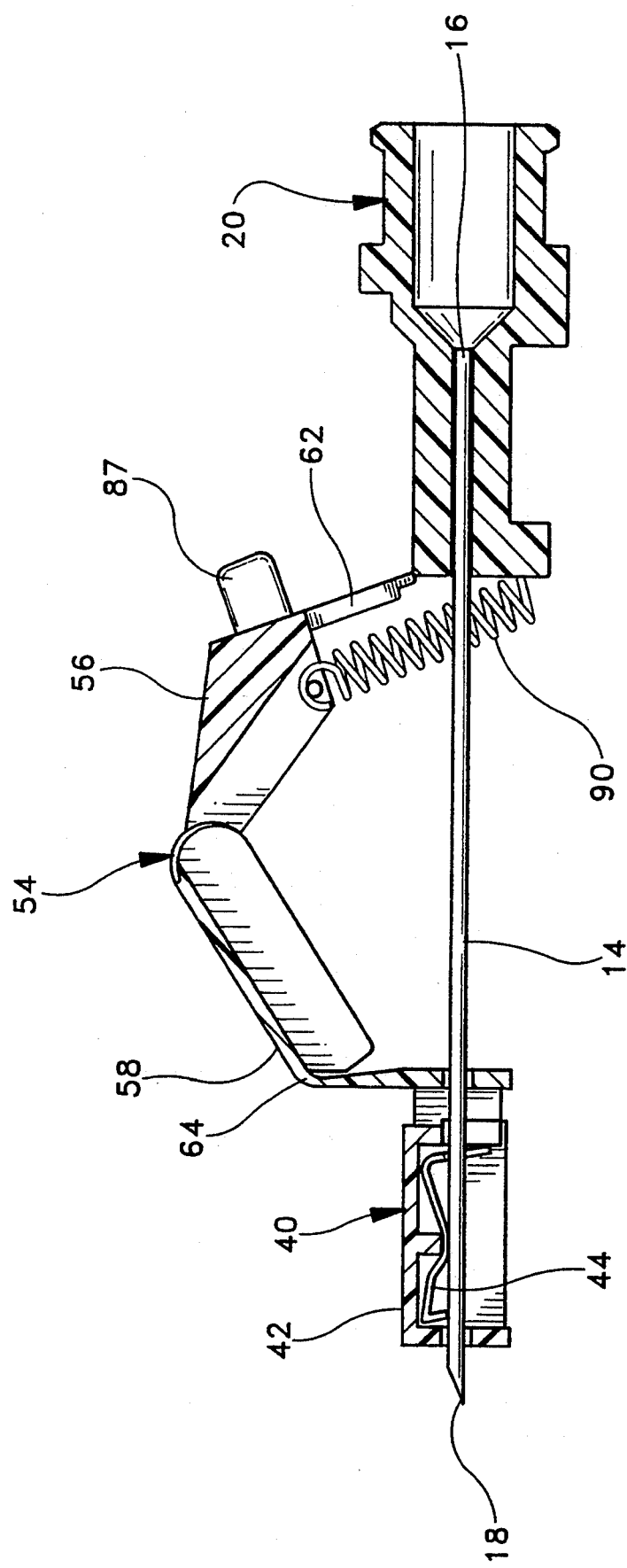
FIG. 6 is a cross-sectional view similar to FIG. 3, but showing an alternate spring.
Figure 8:
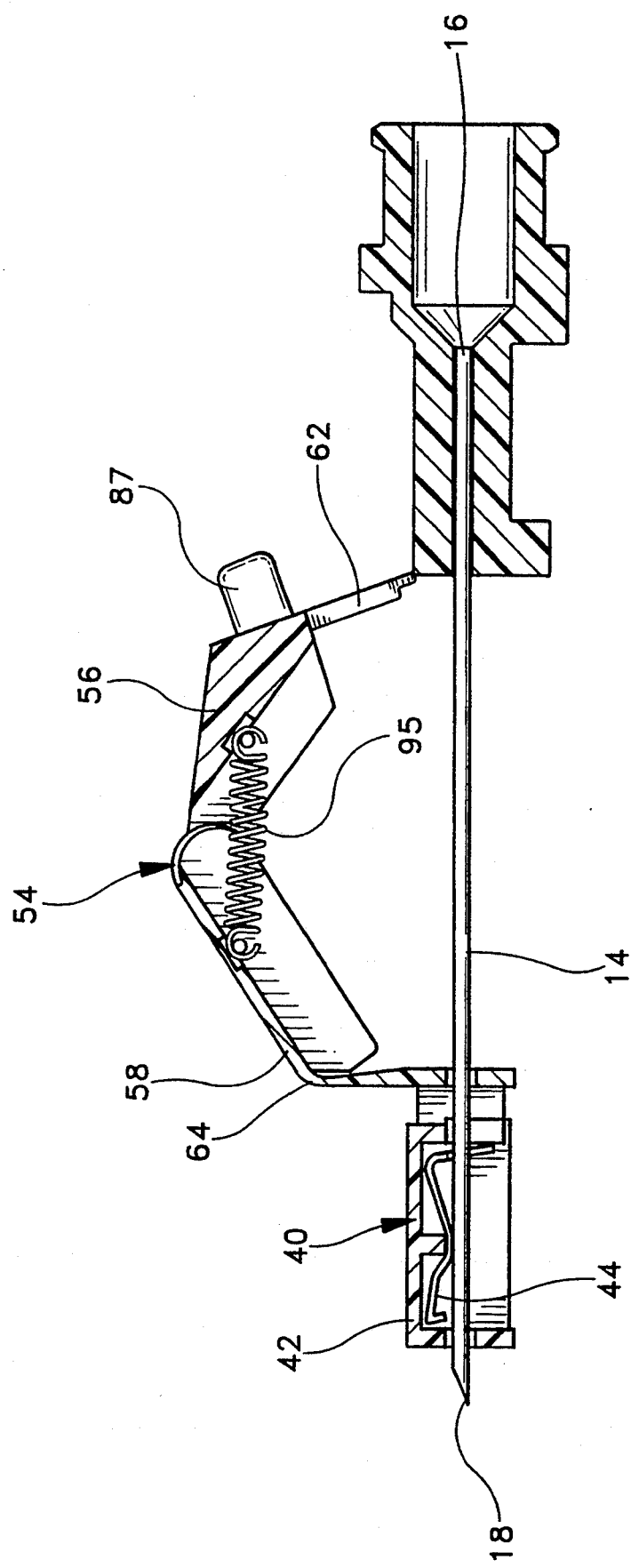
FIG. 8 is a cross-sectional view similar to FIG. 3, but showing an alternate spring.

FIG. 8 illustrates an alternative placement for the coil spring illustrated in the embodiment of FIG. 6. In particular, a coil spring 95 may be connected between proximal segment 56 and distal segment 58. Coil spring 95 is stretched by moving hinged arm 54 from the FIG. 2 orientation to the FIG. 4 orientation. In this embodiment the guard is extended to the position where the distal end of the guard is positioned beyond distal end 18 of the needle cannula. Further motion of the hinged arm assembly causes segments 56 and 58, at hinge pin 60, to bend inwardly to contact the needle cannula and lock into a position much as a weight lifter locks his elbows to hold a weight in an extended position. This embodiment is not a preferred embodiment because the spring does little to propel the guard in a distal direction. However, this embodiment does provide a locked linkage which can eliminate the need for a metal clip in the guard or supplement the clip for additional resistance to backward motion of the guard with respect to the needle.

What is claimed is:

1. A shieldable needle assembly comprising:
a needle cannula having a proximal end and a distal tip;
a guard having a proximal end, an opposed distal end and a side wall extending therebetween, said guard being slidably movable along said needle cannula from a first position substantially adjacent said proximal end of said needle cannula to a second position where said distal tip of said needle cannula is intermediate said opposed proximal and distal ends of said guard;
a hinged arm having proximal and distal segments articulated to one another for movement between a first position where said segments are substantially collapsed onto one another and a second position where said segments are extended from one another, said proximal segment of said hinged arm being articulated to a portion of said needle assembly adjacent said proximal end of said needle cannula, said distal segment of said hinged arm being articulated to said guard, said proximal and distal segments of said hinged arm having respective lengths for permitting said guard to move from said first position to said second position on said needle cannula, and for preventing said guard from moving distally beyond said second position; and
spring means connected to said hinged arm for urging said guard along said needle cannula toward said second position.

2. The shieldable needle assembly of claim 1, wherein said proximal end of said guard comprises a proximal wall having an aperture therethrough, and wherein said needle cannula slidably extends through said aperture of said proximal wall of said guard.

3. The shieldable needle assembly of claim 1, wherein said side wall of said guard is generally annular and is disposed in surrounding relationship to said needle cannula.

4. The shieldable needle assembly of claim 1, wherein said distal end of said guard comprises a distal end wall having an aperture slidably engaged around said needle cannula when said guard is disposed at said first position, said distal end wall being distally beyond said tip of said needle cannula when said guard is in said second position.

5. The shieldable needle assembly of claim 1, wherein said guard comprises a clip retained between said side wall and said needle cannula, said clip being configured to cover said tip when said guard is in said second position on said needle cannula.

6. The shieldable needle assembly of claim 1, further comprising a needle hub securely engaging said proximal end of said needle cannula, said proximal segment of said hinged arm being articulated to said hub.

7. The shieldable needle assembly of claim 6, wherein said hub and said proximal segment of said hinged arm are unitary with one another.

8. The shieldable needle assembly of claim 1, wherein said spring means is substantially unbiased when said guard is in said first position.

9. The shieldable needle assembly of claim 1, wherein said spring means is a coil spring.

10. The shieldable needle assembly of claim 9, wherein said coil spring extends from a portion of said needle assembly adjacent said proximal end of said needle cannula to a location on said proximal segment of said hinged arm.

11. The shieldable needle assembly of claim 1, wherein said spring means comprises an over-center hinge extending unitarily from said proximal segment of said hinged arm and said portion of said needle assembly adjacent said proximal end of said needle cannula.

12. The shieldable needle assembly of claim 1, wherein the proximal and distal segments of the hinged arm each comprise channels dimensioned and disposed to substantially surround said needle cannula when said guard is in said second position.

13. The shieldable needle assembly of claim 12, wherein the channel of one said proximal and distal segments is dimensioned to receive at least a portion of the other of said proximal and distal segments when said guard is in said first position.

14. The shieldable needle assembly of claim 1, wherein said tip of said needle cannula is defined by a bevel having a plane of symmetry, said hinged arm being in said plane of symmetry for indicating orientation of said bevel.

15. The shieldable needle assembly of claim 1, further comprising a hypodermic syringe barrel engaging said proximal end of said needle cannula, said proximal segment of said hinged arm being articulated to said hypodermic syringe barrel.

16. The shieldable needle assembly of claim 5 wherein said clip is made of metal.

17. A shieldable needle assembly comprising:
a needle cannula having a proximal end and a sharply pointed distal tip,
a guard having a proximal end, an opposed distal end and a side wall extending therebetween, said guard being slidably movable along said needle cannula from a first position substantially adjacent said proximal end of said needle cannula to a second position where said distal tip of said needle cannula is intermediate said opposed proximal and distal ends of said guard, said guard including a clip retained between said side wall and said needle cannula, said clip being configured to cover said tip when said guard is in said second position on said needle cannula; and
a hinged arm having proximal and distal segments articulated to one another for movement between a first position where said segments are substantially collapsed onto one another and a second position where said segments are extended from one another, said proximal segment of said hinged arm being articulated to a portion of said needle assembly adjacent said proximal end of said needle cannula, said distal segment of said hinged arm being articulated to said guard, said proximal and distal segments of said hinged arm having respective lengths for permitting said guard to move from said first position to said second position on said needle cannula, and for preventing said guard from moving distally beyond said second position.

18. The shieldable needle assembly of claim 17, further comprising a needle hub securely engaging said proximal end of said needle cannula, said proximal segment of said hinged arm being articulated to said hub.

19. The shieldable needle assembly of claim 18, wherein said hub and said proximal segment of said hinged arm are unitary with one another.

20. The shieldable needle assembly of claim 17, wherein the proximal and distal segments of the hinged arm each comprise channels dimensioned and disposed to substantially surround said needle cannula when said guard is in said second position.

21. The shieldable needle assembly of claim 20, wherein the channel of one said proximal and distal segments is dimensioned to receive at least a portion of the other of said proximal and distal segments when said guard is in said first position.

22. The shieldable needle assembly of claim 17, further comprising a hypodermic syringe barrel integrally engaging said proximal end of said needle cannula, said proximal segment of said hinged arm being articulated to said hypodermic syringe barrel.

23. The shieldable needle assembly of claim 17 wherein said clip is made of metal.

24. A shieldable needle assembly comprising:
a needle cannula having a proximal end and a distal tip;
mounting means securely engaging said proximal end of said needle cannula for providing communication between said needle cannula and a hypodermic syringe barrel;
a guard having a proximal end, an opposed distal end and a side wall extending therebetween, said guard being slidably movable along said needle cannula from a first position substantially adjacent said mounting means to a second position where said distal tip of said needle cannula is intermediate said opposed proximal and distal ends of said guard; and
a hinged arm having proximal and distal segments articulated to one another for movement between a first position where said segments are substantially collapsed onto one another and second position where said segments are extended from one another, said proximal segment of said hinged arm being articulated to said mounting means, said distal segment of said hinged arm being articulated to said guard, said proximal and distal segments of said hinged arm having respective lengths for permitting said guard to move from said first position to said second position on said needle cannula and for preventing said guard from moving distally beyond said second position; and spring means extending between said mounting means and said hinged arm for urging said guard toward said second position.

25. The shieldable needle assembly of claim 24, wherein the proximal segment of said hinged arm is unitary with said mounting means.

26. The shieldable needle assembly of claim 25, wherein said spring means comprises an over-center hinge for urging said guard from a position intermediate said first and second positions into said second position.

27. The shieldable needle assembly of claim 24, wherein said mounting means is a mounting hub for releasable engagement with a hypodermic syringe barrel.

* * * * *

（12) EX PARTE REEXAMINATION CERTIFICATE (7713th)
United States Patent
Sweeney et al.

(10) Number: US 5,348,544 C1
(45) Certificate Issued: Sep. 7, 2010

(54) SINGLE-HANDEDLY ACTUATABLE SAFETY SHIELD FOR NEEDLES

(75) Inventors: Niall Sweeney, Rutherford, NJ (US); Peter W. Bressler, Philadelphia, PA (US); Richard J. Caizza, Barry Lakes, NJ (US)

(73) Assignee: Becton, Dickinson and Company, Franklin Lakes, NJ (US)

Reexamination Request:
No. 90/008,423, Feb. 23, 2007

Reexamination Certificate for:
Patent No.: 5,348,544
Issued: Sep. 20, 1994
Appl. No.: 08/157,780
Filed: Nov. 24, 1993

(51) Int. Cl.
*A61M 5/32* (2006.01)

(52) U.S. Cl. .................. 604/192; 604/198; 128/919
(58) Field of Classification Search .............. None See application file for complete search history.

(56) References Cited

U.S. PATENT DOCUMENTS

| 4,735,618 A | 4/1988 | Hagen |
| 4,911,706 A | 3/1990 | Levitt |
| 4,935,013 A | 6/1990 | Haber et al. |
| 5,176,655 A | 1/1993 | McCormick et al. |

FOREIGN PATENT DOCUMENTS

| NL | 9000909 | 4/1990 |
| WO | WO 90/08564 A1 | 8/1990 |

*Primary Examiner*—Beverly M. Flanagan

(57) ABSTRACT

A safety shield is provided for a medical implement having a needle cannula. The safety shield includes a guard that is slidably movable along the needle cannula from a proximal position where the tip of the needle cannula is exposed to a distal position where the tip of the needle cannula is safety shielded. A hinged arm connects the guard to a hub of the needle cannula or to the medical implement with which the needle cannula is used. The hinged arm can be collapsed upon itself, such that the guard is adjacent the hub of the needle cannula. Alternatively, the hinged arm can be extended to cause the guard to move distally along the needle cannula and into a position for shielding the tip of the needle cannula. A spring may be provided to assist movement of the guard toward the distal shielded position.

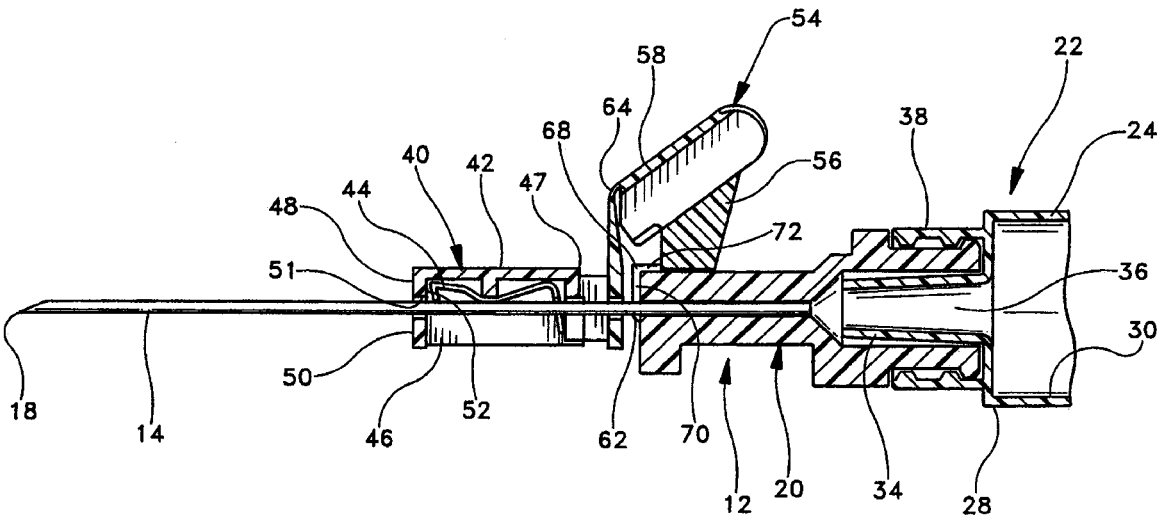

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-7, 12-16, 24, 25, and 27 is confirmed.

Claims 17-23 are cancelled.

Claims 8-11 and 26 were not reexamined.

\* \* \* \* \*